(12) United States Patent
Sun et al.

(10) Patent No.: US 8,541,405 B2
(45) Date of Patent: Sep. 24, 2013

(54) METHODS FOR THE PREPARATION OF IVABRADINE SULFATE AND FORM I CRYSTAL THEREOF

(75) Inventors: Piaoyang Sun, Jiangsu (CN); Yongjiang Chen, Jiangsu (CN); Guangliang Yu, Jiangsu (CN)

(73) Assignee: Jiangsu Hengrui Medicine Co., Ltd., Lianyungang, Jinagsu (CN)

( * ) Notice: Subject to any disclaimer, the term of this patent is extended or adjusted under 35 U.S.C. 154(b) by 140 days.

(21) Appl. No.: 13/144,287

(22) PCT Filed: Oct. 29, 2009

(86) PCT No.: PCT/CN2009/074689
§ 371 (c)(1),
(2), (4) Date: Jul. 12, 2011

(87) PCT Pub. No.: WO2010/081342
PCT Pub. Date: Jul. 22, 2010

(65) Prior Publication Data
US 2011/0275614 A1    Nov. 10, 2011

(30) Foreign Application Priority Data
Jan. 13, 2009    (CN) .......................... 2009 1 0003042

(51) Int. Cl.
*C07D 223/16* (2006.01)
*A61K 31/55* (2006.01)
*A61P 9/10* (2006.01)

(52) U.S. Cl.
USPC ..................................... 514/212.07; 540/523

(58) Field of Classification Search
USPC ..................................... 540/523; 514/212.07
See application file for complete search history.

(56) References Cited

U.S. PATENT DOCUMENTS

| 4,737,495 A | 4/1988 | Bomhard et al. |
| 7,879,842 B2 | 2/2011 | Horvath et al. |
| 7,928,223 B2 * | 4/2011 | Lerestif et al. ............... 540/523 |

FOREIGN PATENT DOCUMENTS

CN    1827600 A    9/2006

OTHER PUBLICATIONS

International Search Report dated Feb. 4, 2010 for corresponding PCT application No. PCT/CN2009/074689.

* cited by examiner

*Primary Examiner* — Bruck Kifle
(74) *Attorney, Agent, or Firm* — Mintz, Levin, Cohn, Ferris, Glovsky and Popeo, P.C.

(57) ABSTRACT

Methods for the preparation of Ivabradine sulfate and form I crystal thereof. In particular, the Ivabradine sulfate and the preparation methods thereof, and the stable form I crystal of Ivabradine sulfate and the preparation methods thereof.

17 Claims, 2 Drawing Sheets

Start angle : 2   End angle : 35   Step Size : 02
Scan speed : 10   Integration time : 12   Target : Cu
Tube current and voltage : 40kV 40mA   Slit : 2 / 4/ 0.5 / 0.2

| Serial number | 2θ | d value | count | Relative intensity | Half-height width | Integration intensity |
|---|---|---|---|---|---|---|
| 1 | 4.760 | 18.549 | 10081 | 99 | 0.200 | 107305 |
| 2 | 14.180 | 6.241 | 5599 | 55 | 0.560 | 166884 |
| 3 | 16.140 | 5.487 | 3712 | 36 | 0.320 | 63224 |
| 4 | 16.940 | 5.230 | 1539 | 15 | 0.320 | 26212 |
| 5 | 18.180 | 4.876 | 2768 | 27 | 0.520 | 76621 |
| 6 | 19.120 | 4.638 | 2478 | 24 | 0.320 | 42202 |
| 7 | 20.040 | 4.427 | 2340 | 23 | 0.760 | 94659 |
| 8 | 20.420 | 4.346 | 2160 | 21 | 1.560 | 179342 |
| 9 | 21.700 | 4.092 | 1749 | 17 | 0.480 | 44687 |
| 10 | 22.560 | 3.938 | 2194 | 21 | 0.320 | 37359 |
| 11 | 23.800 | 3.736 | 2404 | 23 | 0.440 | 56287 |

METHODS FOR THE PREPARATION OF IVABRADINE SULFATE AND FORM I CRYSTAL THEREOF

CROSS-REFERENCE TO RELATED AND PRIORITY APPLICATIONS

The current application is a national phase entry under 35 U.S.C. §371 of international application no. PCT/CN2009/074689, filed on Oct. 29, 2009, which claims priority Chinese application for patent no. 200910003042.X, filed on Jan. 13, 2009. Each of the applications referenced in this paragraph is hereby incorporated by reference herein in its entirety.

FIELD OF THE INVENTION

The present invention relates to a method for the preparation of Ivabradine sulfate and form I crystal thereof, which can be used in the industrial production. The compound of formula (I) obtained according to the method of the invention can be used for the treatment of myocardial ischemia such as angina pectoris and the like.

BACKGROUND OF THE INVENTION

Ivabradine and the addition salts of it with pharmaceutical acceptable acid have highly valuable pharmacological and therapeutic effects, especially bradycardic effects, thus these compounds can be used not only for the treatment or prevention of various clinical symptoms of myocardial ischemia such as angina, myocardial infarction and the associated rhythm disorders, but also for the treatment or prevention of various diseases involving rhythm disorders, especially supraventricular rhythm disorder. In particular the Ivabradine hydrochloride applied by Servier has been approved to be listed in 27 Europe countries by the European medical review administration (EMEA) in November 2005 for the treatment of chronic stable angina pectoris of normal sinus rhythm which has contraindication or intolerance to the beta receptor blocking agent.

U.S. Pat. No. 5,296,482A, 1993 (EP534859A1) describes a synthetic route of Ivabradine in detail.

U.S. Pat. No. 4,737,495 discloses acid which can be used to form addition salts with Ivabradine, especially nontoxic and pharmaceutical acceptable inorganic acids or organic acids. These acids include inorganic acids, such as, hydrochloric acid, hydrobromic acid, sulfuric acid, nitric acid, phosphoric acid, and organic acids, such as acetic acid, propionic acid, maleic acid, fumaric acid, tartaric acid, oxalic acid, benzoic acid, methylsulfonic acid, hydroxylethyl sulfonic acid, benzene sulfonic acid, etc.

Patent CN1583341A, CN1827600A, CN1827599A, CN1827602A, CN1827601A, CN1948292A and CN1948293A disclose the method for the preparation of Ivabradine hydrochloride in α-form, β-form, βd-form, γ-form, γd-form, δ-form, δd-form and the application of their pharmaceutical composition respectively.

But the research result related to various crystal form of Ivabradine addition salts and Ivabradine hydrochloride disclosed in the patents mentioned above is unsatisfactory. Although the U.S. Pat. No. 4,737,495 discloses the scope of pharmaceutical acceptable inorganic or organic acids, which may be suitable for forming the salts, the inventors did not make further research. It is easy for the person skilled in the art to think of the inorganic or organic acids suitable for salinization, however it is valuable to make a further research and find Ivabradine addition salts with better performance.

After extensive study, the present inventors have found that Ivabradine hydrochloride is not the best choice for medicinal Ivabradine additionsalts. Firstly, the methods disclosed in the patents above can not insure to obtain relative pure single crystal form satisfactorily. Ivabradine hydrochloride exists various different crystal structure. The crystal form obtained under various conditions disclosed in the patents above is essentially polycrystal or mixed crystal. Secondly, the stability of various crystals form of Ivabradine hydrochloride is unsatisfactory. The stability of alpha form is relatively good, but the preparation process introduce toluene and 1-methyl-2-pyrrolidone as crystallization solvent that the crystal purity is unsatisfactory and the 1-methyl-2-pyrrolidone is difficult to be removed which can not meet medicinal needs.

In view of the medicinal value of Ivabradine and its salts, it is necessary to find pharmaceutical acceptable Ivabradine salts with more superiority.

SUMMARY OF THE INVENTION

In order to find pharmaceutical acceptable Ivabradine salts with more superiority, the inventors had tested most of the organic and inorganic acids commonly used in pharmacy, to react with Ivabradine to form the salts. The results obtained are clear as expected. That is, the Ivabradine addition salts with good physic-chemical properties including ideal single crystal form, appearance, solubility, stability and the like was obtained. After extensive and deep study, the inventors have found that most organic acids can not form addition salts with Ivabradine with good physic-chemical properties. Although some organic acids form addition salts with Ivabradine, the evaluation is unsatisfactory.

In addition to phosphatic acid, it is easy to obtain addition salts of Ivabradine with inorganic acids. The strong oxidability of nitric acid make the addition salts formed with it unstable. So do the hydrobromic acid and hydrochloric acid. Besides the stability is not very ideal, it also exists polymorphism and it is difficult to get stable single crystal form.

After extensive and deep study, the inventors had surprisingly found that a large number of organic and inorganic acids tested are substantially ineffective except that sulfuric acid and Ivabradine can react to form the corresponding addition salts with good physic-chemical properties, including the ideal single crystal form, appearance, solubility, stability, etc.

Specifically, the present invention relates to Ivabradine sulfate of formula (I).

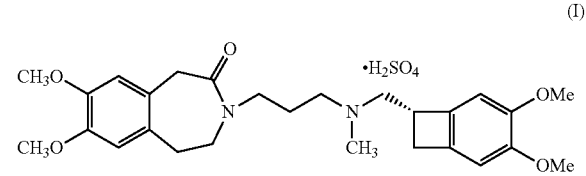

(I)

In a preferable embodiment, the present invention relates to form I crystal of Ivabradine sulfate with X-ray diffraction patterns showed in FIG. 1 which is characteristic in that use Cu-Ka radiation to obtain the X-ray diffraction patterns represented by 2θ angles and interplanar crystal spacing (d value) in which there are characteristic peaks at 4.76 (18.55), 14.18 (6.24), 16.14 (5.49), 16.94 (5.23), 18.18 (4.88), 19.12 (4.64), 20.04 (4.43), 20.42 (4.35), 21.70 (4.09), 22.56 (3.94), 23.80 (3.74).

In another embodiment, the present invention relates to form I crystal of Ivabradine sulfate which is characteristic in that the DSC test of the crystal has distinct fusion absorption peak at 161.3±1° C. as shown in FIG. 2.

In another embodiment, the present invention relates to form I crystal of Ivabradine sulfate which is characteristic in that the range of the melting point of the crystal assayed by capillary tube method is 156.0~158.5° C. and the melting range is less than 2° C.

The process for the preparation of Ivabradine sulfate can be carried out in a conventional solvent, preferably in a polar organic solvent which may be nitriles, such as acetonitrile, alcohols, such as ethanol, isopropyl alcohol, ketones, such as acetone. Moreover the polar organic solvent is preferably alcohols with ethanol as preferred, and ketones, with acetone as preferred.

The process for the preparation of Ivabradine sulfate in the present invention refers to the whole process in which the form I crystal of Ivabradine sulfate was prepared via salifying or crystallization with arbitrary or amorphous form of Ivabradine or Ivabradine sulfate. If necessary, filtering and drying process are also included.

The process for the preparation of form I crystal of Ivabradine sulfate comprises the following steps:

(i) The mixture of arbitrary or amorphous forms of Ivabradine sulfate and moderate polar organic solvents are heated to dissolve, and the solution obtained was stirred or lay and cooled to crystallization; Or the arbitrary or amorphous forms of Ivabradine sulfate was dissolved in methanol and the solvent was evaporated to give an amorphous oil after which the oil was heated to dissolve in polar organic solvents, and the solution obtained was stirred or lay and cooled to crystallization; Or the Ivabradine and sulfuric acid, which the mole ratio is 1:1, was dissolved in moderate polar organic solvent respectively, and then the solution mixture was stirred or lay to crystallization.

(ii) Filtering and washing, and then drying at 40~80° C. in vacuum.

The form I crystal of Ivabradine sulfate with good crystal purity and stability, obtained by the process of the invention is especially suitable for the clinical use as medicinal addition salt.

DETAILED DESCRIPTION OF THE INVENTION

The present invention is illustrated by the following examples in detail which in no way should be construed as limiting the scope of the present invention.
Experimental Instruments
X-ray diffraction spectrum
Instrument type: D/Max-RA Japan RigakuX-ray powder diffraction
Ray: monochromatic Cu-Ka rays ($\lambda$=1.5418 Å)
Scanning mode: $\theta/2\theta$, Angular scan of 3-40°
Voltage: 30KV, Electric Current: 50 mA
Thermal analysis (DSC)
Instrument type: Perkin-Elmer Pyris 7 Series Thermal Analysis System
Purging gas: Nitrogen
Heating rate: DSC: 10.0° C./min
Temperature range: DSC:50-300° C.

Example 1

Figure 1:
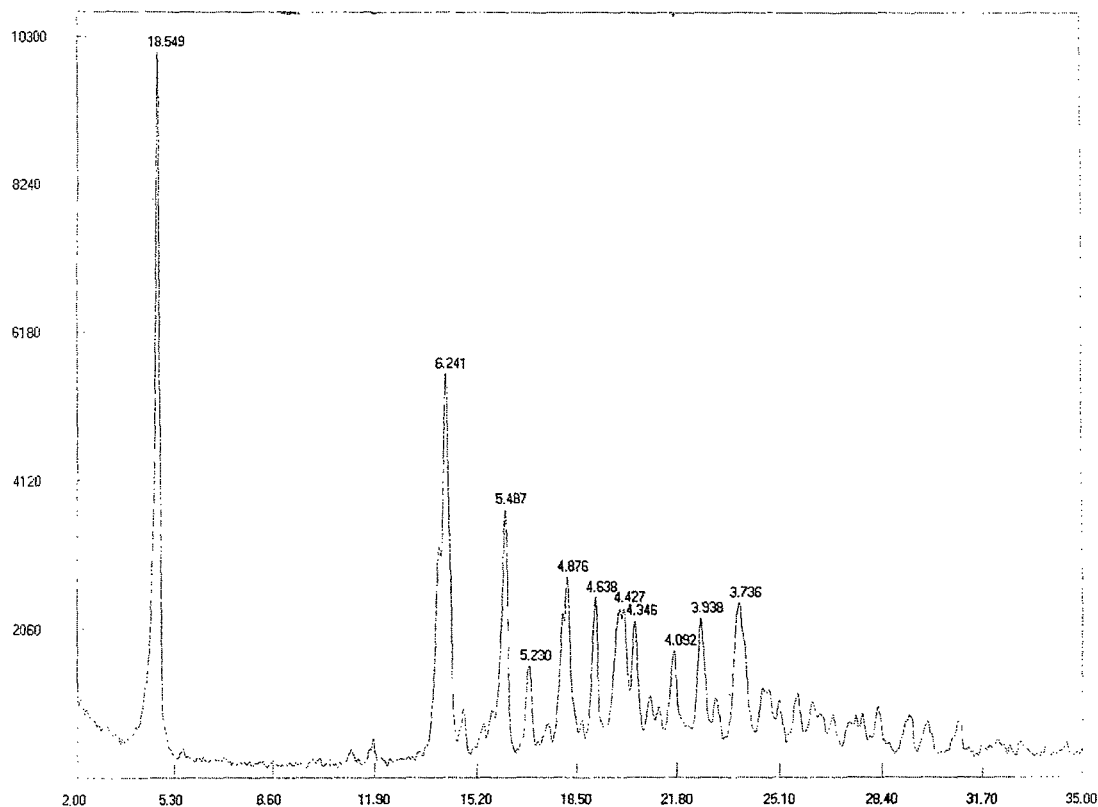
FIG. 1 shows the X-ray powder diffraction pattern for the form I crystal of Ivabradine sulfate.
Figure 2:
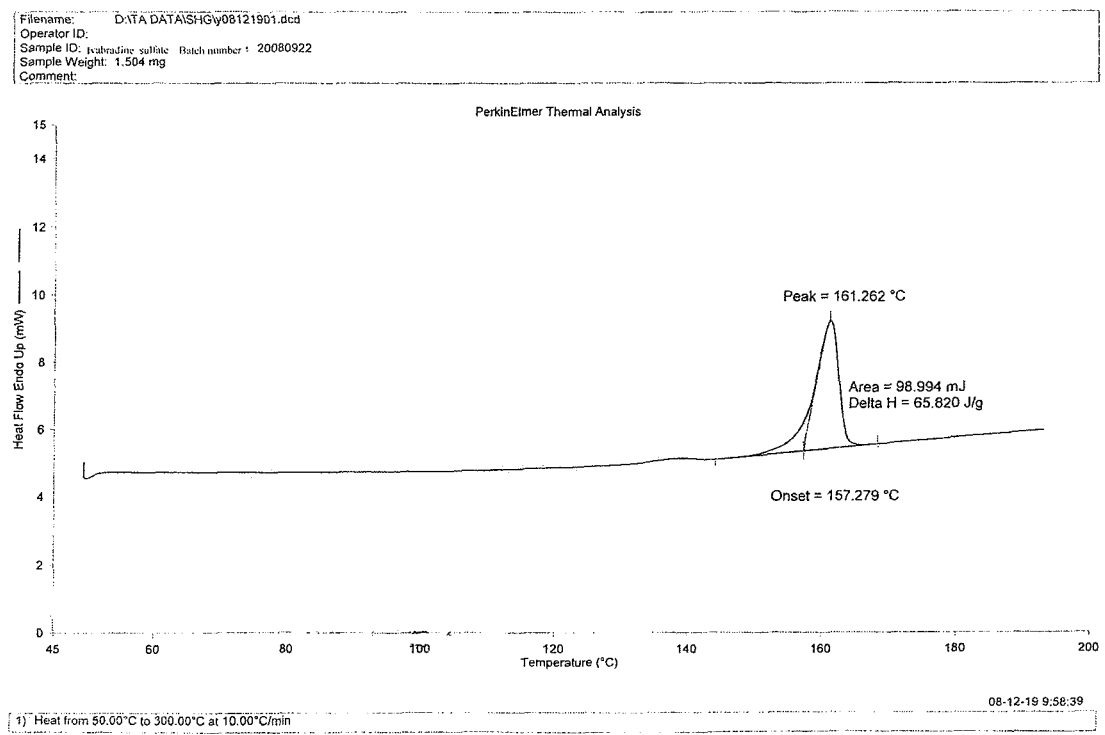
FIG. 2 shows the Differential Scanning Caborimetry pattern for the form I crystal of Ivabradine sulfate.

4.3 g of Ivabradine sulfate was dissolved in 100 ml of acetone, then 30 ml of acetone containing 1 g of sulfuric acid was added. The obtained mixture was stirred and white crystals were precipitated from the reaction solution. The resulting precipitate was collected by filtration, washed with acetone and then dried at 60° C. in vacuum for 3 hours to obtain 4.8 g of Ivabradine sulfate. Melting point was determined by capillary crystalline approach at 156~158° C. Water content is 0.8%. The pH of the Ivabradine sulfate aqueous is about 1.8 (C=1%). Yield: 90.5%. X-ray pattern is showed in FIG. 1 which the crystal form is form I. DSC pattern is showed in FIG. 2, with sharp molten absorption peak at 161.3° C.

Example 2

4.3 g of Ivabradine sulfate was dissolved in 100 ml of acetone, then 30 ml of acetone containing 0.4 g of sulfuric acid was added. The obtained mixture was stirred and white crystals were precipitated from the reaction solution. The resulting precipitate was collected by filtration, washed with acetone and then dried at 60° C. in vacuum for 3 hours to obtain 1.2 g of Ivabradine sulfate. Melting point was determined by capillary crystalline approach at 156~158° C. Water content is 0.8%. The pH of the Ivabradine sulfate aqueous is about 1.8 (C=1%). Yield: 55.5%. It is form I crystal of Ivabradine sulfate judged by X-ray and DSC patterns.

Example 3

2.0 g of the form I crystal of Ivabradine sulfate (prepared by example 1) was dissolved in 50 ml of methanol. The solvent was concentrated in vacuum to dryness, and 65 ml of acetone was added. The mixture was heated in water bath to dissolve and then stirred to precipitate the white crystals. After cooling to room temperature, the resulting precipitate was collected by filtration, washed by acetone and then dried at 60° C. in vacuum for 3 hours to obtain 1.82 g of Ivabradine sulfate. Water content is 0.7%. Yield: 91.0%. It is form I crystal of Ivabradine sulfate judged by X-ray and DSC patterns. The data of stability test was shown in table 1.

Example 4

2.0 g of the form I crystal of Ivabradine sulfate (prepared by example 1) was dissolved in 50 ml of methanol. The solvent was concentrated in vacuum to dryness, and 25 ml of ethanol was added. The mixture was heated in water bath to dissolve, and then stirred to precipitate the white crystals. After cooling to room temperature, the resulting precipitate was collected by filtration, washed by ethanol and then dried at 60° C. in vacuum for 3 hours to obtain 1.23 g of Ivabradine sulfate. Melting point was determined by capillary crystalline approach at 156.5~158.5° C. Water content is 0.7%. Yield: 61.5%. It is form I crystal of Ivabradine sulfate judged by X-ray and DSC patterns.

Example 5

The stability investigation of different Ivabradine hydrochloride crystal form: three different solvents crystallization of samples were obtained in turn according to the method of example 4 except that Ivabradine sulfate is substituted with Ivabradine hydrochloride and ethanol is substituted with acetonitrile, ethyl acetate, acetone.

Moreover, α-form crystal samples can be obtained using toluene, N-methyl pyrrole as crystallization solvents according to the method disclosed in CN1583341A.

The four samples obtained above and the form I crystal of Ivabradine sulfate prepared in example 1 were placed opening in the air to test the stability in various conditions including illumination (4500 Lux), heating (60° C.), humidity (RH 90%). The investigation time is five and ten days and the HPLC analysis results are shown in table 1.

TABLE 1

The comparing of stability of Ivabradine sulfate and Ivabradine hydrochloride

| Batch number | Solvent | Time (Day) | Light | 60° C. | RH90% |
|---|---|---|---|---|---|
| Ivabradine | Acetone | 0 | 99.46% | 99.46% | 99.46% |
| sulfate | | 5 | 99.42% | 99.42% | 99.28% |
| 20080922 | | 10 | 99.39% | 99.40% | 99.19% |
| Ivabradine | Toluene/ | 0 | 99.54% | 99.54% | 99.54% |
| sulfate | N- | 5 | 99.47% | 99.50% | 99.23% |
| 20080618 | methyl pyrrolidone | 10 | 99.42% | 99.46% | 99.00% |
| Ivabradine | Acetonitrile | 0 | 99.56% | 99.56% | 99.56% |
| hydrochloride | | 5 | 97.45% | 98.74% | 99.03% |
| 20080908 | | 10 | 94.91% | 99.04% | 98.61% |
| Ivabradine | Ethyl | 0 | 99.55% | 99.55% | 99.55% |
| hydrochloride | acetate | 5 | 98.88% | 99.31% | 99.10% |
| 20080911 | | 10 | 98.07% | 99.12% | 98.42% |
| Ivabradine | Acetone | 0 | 99.57% | 99.57% | 99.57% |
| hydrochloride | | 5 | 99.29% | 99.36% | 99.20% |
| 20080912 | | 10 | 98.87% | 99.05% | 98.91% |

The results show that the stability of the form I crystal of Ivabradine sulfate and the α-form crystal of Ivabradine hydrochloride are similar under the light and heat condition without statistically significant. The form I crystal of Ivabradine sulfate is more stable than the α-form crystal of Ivabradine hydrochloride under high moisture conditions. Compared with the several polymorphism or mixed crystal, which come from the crystallization solvent of acetonitrile, ethyl acetate, acetone, the stability of the form I crystal of Ivabradine sulfate improved significantly under various conditions.

What is claimed is:

1. A form I crystal of Ivabradine sulfate of formula (I),

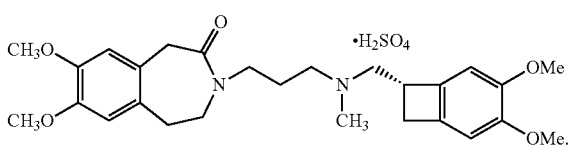

(I)

the crystal being characterized in that using CuKα radiation to obtain X-ray diffraction patterns represented by 2θ angles and interplanar crystal spacing (d value), the obtained X-ray diffraction patterns comprise characteristic peaks at 4.76 (18.55), 14.18 (6.24), 16.14 (5.49), 16.94 (5.23), 18.1 (4.88), 19.12 (4.64), 20.04 (4.43), 20.42 (4.35), 21.70 (4.09), 22.56 (3.94), and 23.80 (3.74).

2. A form I crystal of Ivabradine sulfate as in claim 1, wherein a differential scanning calorimetry (DSC) curve obtained for the form I crystal of Ivabradine sulfate, characterized in that the DSC of the crystal comprises a distinct fusion absorption peak at 161.3±1° C.

3. A form I crystal of Ivabradine sulfate as in claim 1, wherein the form I crystal of Ivabradine sulfate is further characterized in that a melting point of the form I crystal as assayed by a capillary tube method is in a range of 156.0 to 158.5° C. and a melting range of the form I crystal is less than 2° C.

4. A method for preparing a form I crystal of Ivabradine sulfate comprising:
heating a mixture of arbitrary or amorphous forms of Ivabradine sulfate and one or more moderate polar organic solvents to dissolve the arbitrary or amorphous forms of Ivabradine sulfate
stirring and/or laying and cooling the mixture to crystallization; and
filtering and washing, and then drying at a drying temperature in a range of 40~80° C. in vacuum;
wherein the crystal being characterized in that using CuKα radiation to obtain X-ray diffraction patterns represented by 2θ angles and interplanar crystal spacing (d value), the obtained X-ray diffraction patterns comprise characteristic peaks at 4.76 (18.55), 14.18 (6.24), 16.14 (5.49), 16.94 (5.23), 18.1 (4.88), 19.12 (4.64), 20.04 (4.43), 20.42 (4.35), 21.70 (4.09), 22.56 (3.94), and 23.80 (3.74).

5. A method for preparing a form I crystal of Ivabradine sulfate comprising:
dissolving one or more of arbitrary and amorphous forms of Ivabradine sulfate in a solvent comprising methanol;
concentrating the solvent to obtain an amorphous oil; heating the amorphous to dissolve the amorphous oil in a second solvent composition comprising one or more polar organic solvents;
stirring and/or laying and cooling the second solvent mixture to crystallization; and
filtering and washing, and then drying at a drying temperature in a range of 40~80° C. in vacuum;
wherein the crystal being characterized in that using CuKα radiation to obtain X-ray diffraction patterns represented by 2θ angles and interplanar crystal spacing (d value), the obtained X-ray diffraction patterns comprise characteristic peaks at 4.76 (18.55), 14.18 (6.24), 16.14 (5.49), 16.94 (5.23), 18.1 (4.88), 19.12 (4.64), 20.04 (4.43), 20.42 (4.35), 21.70 (4.09), 22.56 (3.94), and 23.80 (3.74).

6. A method for preparing a form I crystal of Ivabradine sulfate comprising:
dissolving Ivabradine and sulfuric acid at a mole ratio of approximately 1:1 in a solvent composition comprising a moderate polar organic solvent to form a mixture;
mixing and stirring and/or laying the mixture to crystallization; and
filtering and washing, and then drying at a drying temperature in a range of approximately 40~80° C. in vacuum;
wherein the crystal being characterized in that using CuKα radiation to obtain X-ray diffraction patterns represented by 2θ angles and interplanar crystal spacing (d value), the obtained X-ray diffraction patterns comprise characteristic peaks at 4.76 (18.55), 14.18 (6.24), 16.14 (5.49), 16.94 (5.23), 18.1 (4.88), 19.12 (4.64), 20.04 (4.43), 20.42 (4.35), 21.70 (4.09), 22.56 (3.94), and 23.80 (3.74).

7. A method as in claim 4, wherein the one or more moderate polar organic solvents comprise at least one of methanol, ethanol, isopropyl alcohol, acetone or acetonitrile, preferably acetone or ethanol.

8. A method of treating stable angina pectoris using a form I crystal of Ivabradine sulfate according to claim 1 comprising:
preparing a medicament comprising the form I crystal of Ivabradine sulfate, wherein the crystal being characterized in that using CuKα radiation to obtain X-ray diffraction patterns represented by 2θ angles and interplanar crystal spacing (d value), the obtained X-ray diffraction patterns comprise characteristic peaks at 4.76 (18.55), 14.18 (6.24), 16.14 (5.49), 16.94 (5.23), 18.1 (4.88), 19.12 (4.64), 20.04 (4.43), 20.42 (4.35), 21.70 (4.09), 22.56 (3.94), and 23.80 (3.74).

9. A pharmaceutical composition comprising:
a therapeutically effective amount of the form I crystal of Ivabradine sulfate according to claim 1; and
one or more pharmaceutically acceptable carriers, wherein the crystal being characterized in that using CuKα radiation to obtain X-ray diffraction patterns represented by 2θ angles and interplanar crystal spacing (d value), the obtained X-ray diffraction patterns comprise characteristic peaks at 4.76 (18.55), 14.18 (6.24), 16.14 (5.49), 16.94 (5.23), 18.1 (4.88), 19.12 (4.64), 20.04 (4.43), 20.42 (4.35), 21.70 (4.09), 22.56 (3.94), and 23.80 (3.74).

10. A method as in claim 5, wherein the one or more moderate polar organic solvents comprise at least one of methanol, ethanol, isopropyl alcohol, acetone or acetonitrile, preferably acetone or ethanol.

11. A method as in claim 6, wherein the moderate polar organic solvent comprises at least one of methanol, ethanol, isopropyl alcohol, acetone or acetonitrile, preferably acetone or ethanol.

12. A method as in claim 4, wherein the form I crystal of Ivabradine sulfate is characterized in that a differential scanning calorimetry (DSC) curve obtained for the form I crystal of Ivabradine sulfate comprises a distinct fusion absorption peak at 161.3±1° C.

13. A method as in claim 4, wherein the form I crystal of Ivabradine sulfate is characterized in that a melting point of the form I crystal as assayed by a capillary tube method is in a range of 156.0 to 158.5° C. and a melting range of less than 2° C.

14. A method as in claim 5, wherein the form I crystal of Ivabradine sulfate is characterized in that a differential scanning calorimetry (DSC) curve obtained for the form I crystal of Ivabradine sulfate comprises a distinct fusion absorption peak at 161.3±1° C.

15. A method as in claim 5, wherein the form I crystal of Ivabradine sulfate is characterized in that a melting point of the form I crystal as assayed by a capillary tube method in a range of 156.0 to 158.5° C. and a melting range of less than 2° C.

16. A method as in claim 6, wherein the form I crystal of Ivabradine sulfate is characterized in that a differential scanning calorimetry (DSC) curve obtained for the form I crystal of Ivabradine sulfate comprises a distinct fusion absorption peak at 161.3±1° C.

17. A method as in claim 6, wherein the form I crystal of Ivabradine sulfate is characterized in that a melting point of the form I crystal as assayed by a capillary tube method in a range of 156.0 to 158.5° C. and a melting range of the form I crystal is less than 2° C.

* * * * *